US012390370B2

(12) United States Patent
Vaughan et al.

(10) Patent No.: US 12,390,370 B2
(45) Date of Patent: Aug. 19, 2025

(54) TYMPANOSTOMY TUBE

(71) Applicant: AVENTAMED DESIGNATED ACTIVITY COMPANY, Bishopstown (IE)

(72) Inventors: John Vaughan, Blarney (IE); Olive O'Driscoll, Kinsale (IE); Carol Grimes, Skerries (IE)

(*) Notice: Subject to any disclaimer, the term of this patent is extended or adjusted under 35 U.S.C. 154(b) by 399 days.

(21) Appl. No.: 17/773,570

(22) PCT Filed: Oct. 29, 2020

(86) PCT No.: PCT/EP2020/080449
§ 371 (c)(1),
(2) Date: Apr. 29, 2022

(87) PCT Pub. No.: WO2021/084032
PCT Pub. Date: May 6, 2021

(65) Prior Publication Data
US 2022/0370253 A1    Nov. 24, 2022

(30) Foreign Application Priority Data
Nov. 1, 2019   (EP) .................................... 19206774

(51) Int. Cl.
*A61F 11/20*    (2022.01)
*A61F 2/00*    (2006.01)
*A61F 2/958*    (2013.01)

(52) U.S. Cl.
CPC ............ *A61F 11/202* (2022.01); *A61F 2/958* (2013.01); *A61F 2002/0081* (2013.01);
(Continued)

(58) Field of Classification Search
CPC .................... A61F 11/202; A61F 2/958; A61F 2002/0081; A61F 2210/0014;
(Continued)

(56) References Cited

U.S. PATENT DOCUMENTS 4,744,792 A  *  5/1988  Sander .................. A61F 11/202
                                                      623/10
4,964,850 A  *  10/1990  Bouton ............... A61M 27/002
                                                     604/106
(Continued)

FOREIGN PATENT DOCUMENTS

KR    1020190117257 A    10/2019
WO         9511634 A1    5/1995
(Continued)

OTHER PUBLICATIONS

International Search Report, International application No. PCT/EP2020/080449. Date of mailing: Jan. 26, 2021. European Patent Office, Rijswijk, NL.
(Continued)

*Primary Examiner* — Katherine H Schwiker
(74) *Attorney, Agent, or Firm* — David N. Villalpando; Jacqueline Cohen

(57) ABSTRACT

A fluidic bridging tube (1), for bridging membranes in the human or animal body allowing the passage of fluid, has a proximal flange (2), an inter lumen connector (3) with a lumen (5) and a distal flange (4). The tube comprises a metal skeleton or scaffold structure (51) and a surrounding polymer which is softer than the scaffold structure. The scaffold structure (51) has a tubular mesh providing structural strength to the inter lumen connector. The tubular mesh has members (61) defining substantial rectangular mesh apertures, and distal crowns (64). At its proximal end the scaffold structure comprises spines (68) extending from a proximal tubular mesh rim (63). The spines provide structural strength to the proximal flange (2). In the preferred embodiment the tube is a tympanostomy tube. A method of manufacturing the tube comprises providing the scaffold structure and over-moulding the outer material to form the shape of the
(Continued)

proximal flange, the inter lumen connector with a lumen, and the distal flange.

17 Claims, 5 Drawing Sheets

(52) U.S. Cl.
CPC .......... *A61F 2210/0014* (2013.01); *A61F 2220/0008* (2013.01); *A61F 2230/0019* (2013.01); *A61F 2230/0069* (2013.01); *A61F 2250/0026* (2013.01); *A61F 2250/0029* (2013.01); *A61F 2250/0039* (2013.01)

(58) Field of Classification Search
CPC ...... A61F 2220/0008; A61F 2230/0019; A61F 2230/0069; A61F 2250/0026; A61F 2250/0029; A61F 2250/0039
See application file for complete search history.

(56) References Cited

U.S. PATENT DOCUMENTS

| | | | |
|---|---|---|---|
| 6,406,453 B1 | 6/2002 | Goode et al. |
| 6,692,455 B2 | 2/2004 | Goode et al. |
| 6,936,023 B2 | 8/2005 | Goode et al. |
| 7,097,661 B2 | 8/2006 | Perry |
| 8,197,433 B2 | 6/2012 | Cohen |
| 8,332,999 B2 | 12/2012 | Karling et al. |
| 8,480,610 B1 | 7/2013 | Hill |
| 8,480,611 B1 | 7/2013 | Alshemari |
| 8,529,495 B1 | 9/2013 | Alshemari |
| D707,822 S | 6/2014 | Clopp et al. |
| 8,795,290 B2 | 8/2014 | Konstorum et al. |
| 8,864,774 B2 | 10/2014 | Liu et al. |
| 8,945,142 B2 | 2/2015 | Schaeffer et al. |
| 9,011,363 B2 | 4/2015 | Clopp et al. |
| 9,023,059 B2 | 5/2015 | Oushin et al. |
| 9,345,473 B2 | 5/2016 | Fisher |
| 9,370,448 B2 | 6/2016 | Loushin et al. |
| 9,504,490 B2 | 11/2016 | Konstorum et al. |
| 9,707,131 B2 | 7/2017 | Shahoian |
| 9,770,366 B2 | 9/2017 | Liu et al. |
| 9,782,298 B2 | 10/2017 | Loushin et al. |
| 10,130,515 B2 | 11/2018 | Kaplan et al. |
| 10,258,776 B2 | 4/2019 | Clifford et al. |
| 10,588,782 B2 | 3/2020 | Skovlund |
| 10,595,848 B2 | 3/2020 | Woodard et al. |
| 10,610,412 B2 | 4/2020 | Liu et al. |
| 10,624,792 B2 | 4/2020 | Loushin et al. |
| 10,632,017 B2 | 4/2020 | Girotra et al. |
| 10,653,446 B2 | 5/2020 | Andreas et al. |
| 10,653,561 B2 | 5/2020 | Andreas et al. |
| 10,695,224 B2 | 6/2020 | Loushin et al. |
| 10,736,785 B2 | 8/2020 | Clopp |
| 10,751,219 B2 | 8/2020 | Vaughan et al. |
| 10,765,560 B2 | 9/2020 | Clopp et al. |
| 10,792,189 B2 | 10/2020 | Leland et al. |
| 10,835,422 B2 | 11/2020 | Clopp et al. |
| 10,881,506 B2 | 1/2021 | Angelillo et al. |
| 10,918,525 B2 | 2/2021 | Andreas et al. |
| 10,966,866 B2 | 4/2021 | Van et al. |
| 11,116,949 B2 | 9/2021 | Lee et al. |
| 2007/0183613 A1* | 8/2007 | Juneau ................. H04R 25/656 |
| | | | 381/328 |
| 2011/0152875 A1 | 6/2011 | Gonzales |
| 2012/0179187 A1 | 7/2012 | Loushin et al. |
| 2014/0094733 A1* | 4/2014 | Clopp ................... A61F 11/20 |
| | | | 604/8 |
| 2014/0276906 A1 | 9/2014 | Andreas et al. |
| 2015/0164695 A1 | 6/2015 | Liu et al. |
| 2018/0296243 A1 | 10/2018 | Hanson et al. |
| 2019/0038469 A1 | 2/2019 | Imran et al. |
| 2019/0192349 A1 | 6/2019 | Vaughan et al. |
| 2020/0022842 A1 | 1/2020 | Labib et al. |
| 2020/0163800 A1 | 5/2020 | Skovlund |
| 2020/0237559 A1 | 7/2020 | Loushin et al. |
| 2020/0237560 A1 | 7/2020 | Andreas et al. |
| 2020/0281772 A1 | 9/2020 | Loushin et al. |
| 2021/0052868 A1 | 2/2021 | Goldfarb et al. |
| 2021/0169697 A1 | 6/2021 | Vaughan et al. |

FOREIGN PATENT DOCUMENTS

| | | |
|---|---|---|
| WO | 2013113022 A1 | 8/2013 |
| WO | 2014075949 A1 | 5/2014 |
| WO | 2015095214 A1 | 6/2015 |
| WO | 2016128071 A1 | 8/2016 |
| WO | 2019086608 A1 | 5/2019 |
| WO | 2019183295 A1 | 9/2019 |

OTHER PUBLICATIONS

Written Opinion of the International Searching Authority, International application No. PCT/EP2020/080449. Date of mailing: Jan. 26, 2021. European Patent Office, Munich, DE.

* cited by examiner

TYMPANOSTOMY TUBE

INTRODUCTION

The invention relates to tympanostomy tubes, and to other tubes for passage of fluid within the body across walls or membranes having broadly similar characteristics to the tympanic membrane. Examples are tubes for bridging membranes in the body such as ocular drainage devices.

WO2019/086608 (AventaMed Designated Activity Company) describes a tympanostomy tube and placement device. The tube has a proximal flange which acts as a stop or depth perception during placement, an inter lumen connector for passage of fluid across the tympanic membrane, and a distal flange which is folded during deployment and un-folds when located on the distal side of the membrane. It is desirable in this case, and for many other placement methodologies, that the distal flange be more flexible than the proximal flange to achieve effective deployment.

The invention is directed towards achieving a tympanostomy tube which has improved flexural and strength characteristics for both deployment and use.

SUMMARY

Also, we describe a fluidic bridging tube for use in a human or animal, the tube comprising a proximal flange, an inter lumen connector with a lumen, and a distal flange, wherein the tube comprises a scaffold structure and an outer material which is softer than the scaffold structure and fully or partially surrounds the scaffold structure.

Preferably, the tube is a tympanostomy tube.

Preferably, the scaffold structure comprises a tubular mesh extending through at least some of the inter lumen connector. Preferably, the tubular mesh has a member defining substantially curved rectangular mesh apertures, which optionally have substantially equal sides. Preferably, the tubular mesh comprises crowns at its distal end.

Preferably, the tubular mesh comprises a rim without apertures at its proximal end.

Preferably, the scaffold structure comprises spines extending with a radial directional component to provide structural support for the proximal flange at least. Preferably, the scaffold structure comprises spines which are substantially equally separated radially.

Preferably, the scaffold structure comprises material selected from Stainless Steel, Nitinol, titanium, or a polymer.

Preferably, the outer material comprises medical grade silicone rubber.

Preferably, the outer material is over-moulded on the scaffold structure.

Preferably, the scaffold structure is completely surrounded (enveloped) by the outer material.

Preferably, the distal flange does not include any part of the scaffold structure.

We also describe a method of manufacturing a fluidic bridging tube of any example described herein, the method comprising providing the scaffold structure and over-moulding the outer material to form the shape of the proximal flange, the inter lumen connector with a lumen, and the distal flange.

DETAILED DESCRIPTION OF THE INVENTION

The invention will be more clearly understood from the following description of some embodiments thereof, given by way of example only with reference to the accompanying drawings in which.

Figure 1:
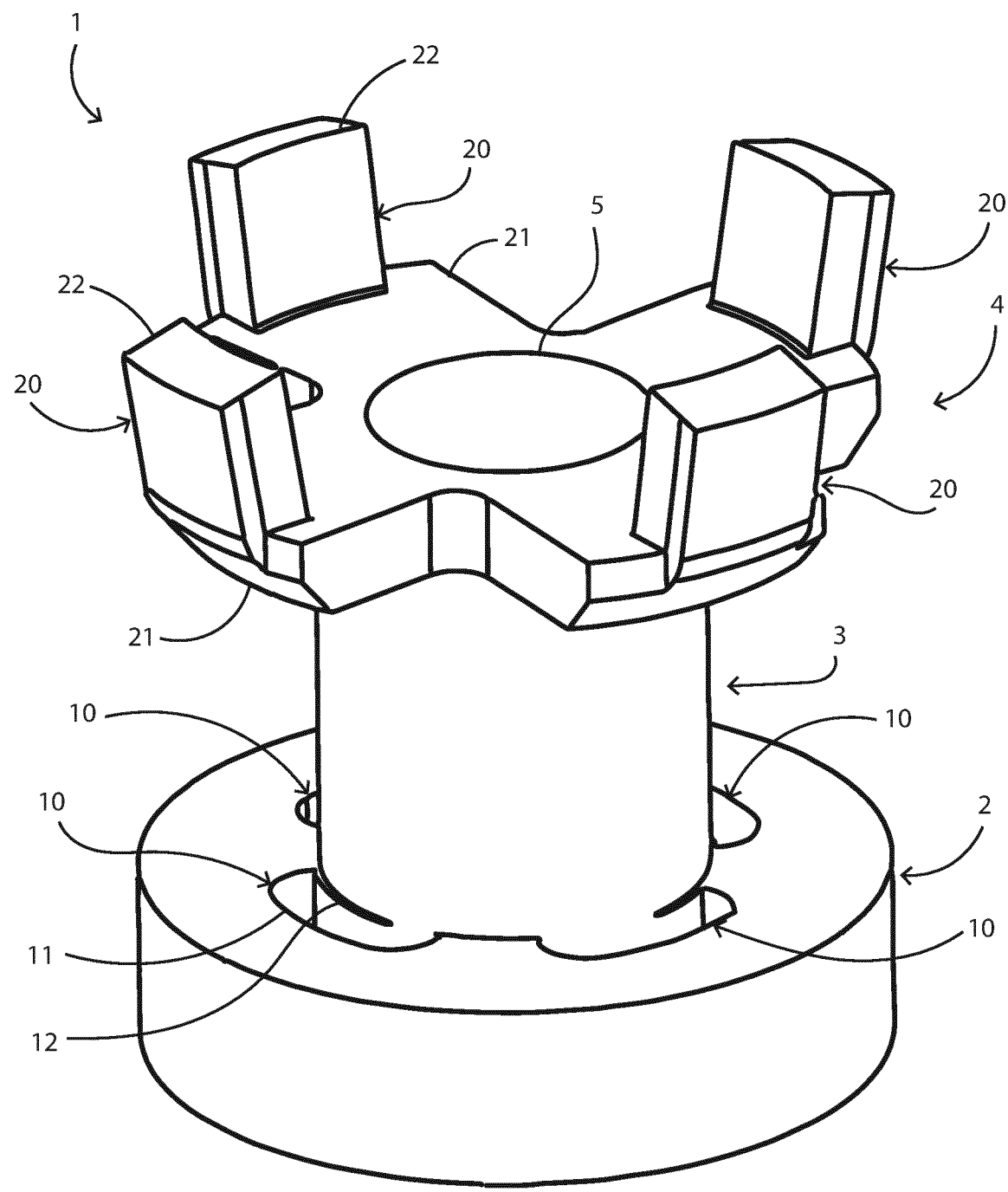
FIG. 1 is a perspective view of a tympanostomy tube.

Referring to FIG. 1 a tympanostomy tube 1 comprises:
a proximal flange 2,
an inter lumen connector 3 forming a lumen 5, and
a distal flange 4.

The proximal flange 2 has four equally-spaced through holes for retainer fingers of a placement device aligned with tabs 20 of the distal flange 4. In other examples, there may be different numbers and/or spacing of through holes and associated tabs in the distal flange. The holes 10 have curved outer surfaces and circumferentially curved inner surfaces 12. Each tab 20 has a radial part 21 and an axial part 22, the latter being at an acute angle of about 10° to the longitudinal axis of the tube 1. The longitudinal axis is the central axis of the lumen 5.

The tube 1 is deployed in a manner described in WO2019/086608, achieved by a placement device having longitudinal fingers which extend through the holes 10 and press radially inwardly the distal flange 4, more specifically the tab 20 radial parts 21 and axial parts 22. When the placement device's needle has pierced the tympanic membrane the proximal flange acts as a stop or depth perception of the device from the tympanic membrane, with its distally-facing face in contact or near-contact with the tympanic membrane. The placement device retainer fingers and needle are then retracted, causing the distal flange 4 tabs 20 to spring out to the radial position illustrated in FIG. 1, thereby securing the tube 1 in place across the membrane.

Figure 2:
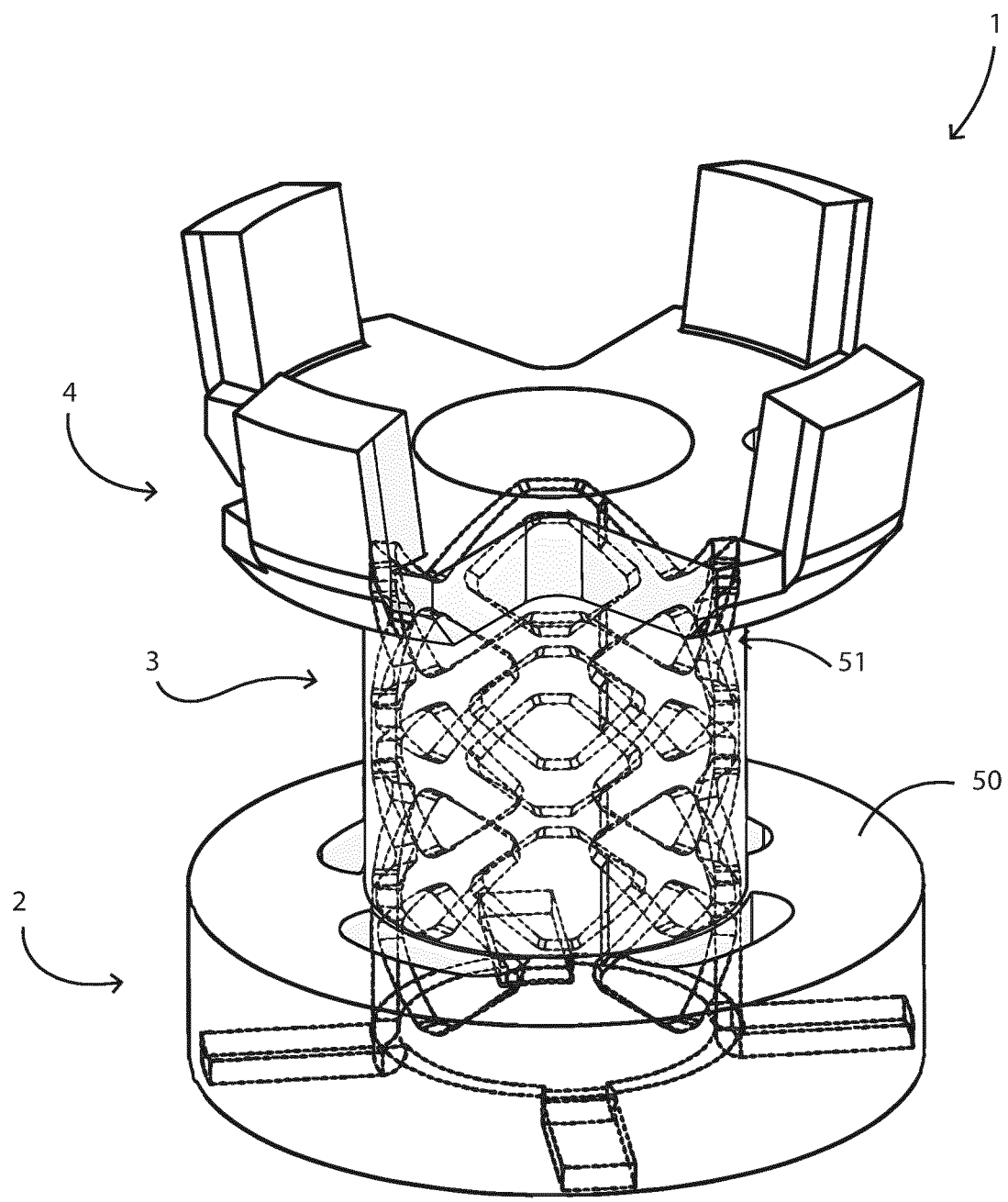
FIG. 2 is an illustration showing the internal structure with hidden lines.

As shown in FIG. 2 the composition of the tube 1 comprises an internal skeleton or scaffold structure 51 of metal (or in other examples of suitable rigid material such as a rigid polymer), and a surrounding outer material 50 which is softer.

In this case the scaffold structure 51 material is Stainless Steel and the surrounding outer material 50 is a silicone over-mould. In other examples the skeleton may include titanium or other suitable material, which is also more rigid than the outer material.

The outer material 50 is preferably over-moulded, and it preferably comprises a polymer of more resilient and less rigid material than the scaffold. The over-mould material in this example is a liquid silicone rubber of medical grade, preferably having a Shore A hardness in the range of 50 to 90.

Figure 3:
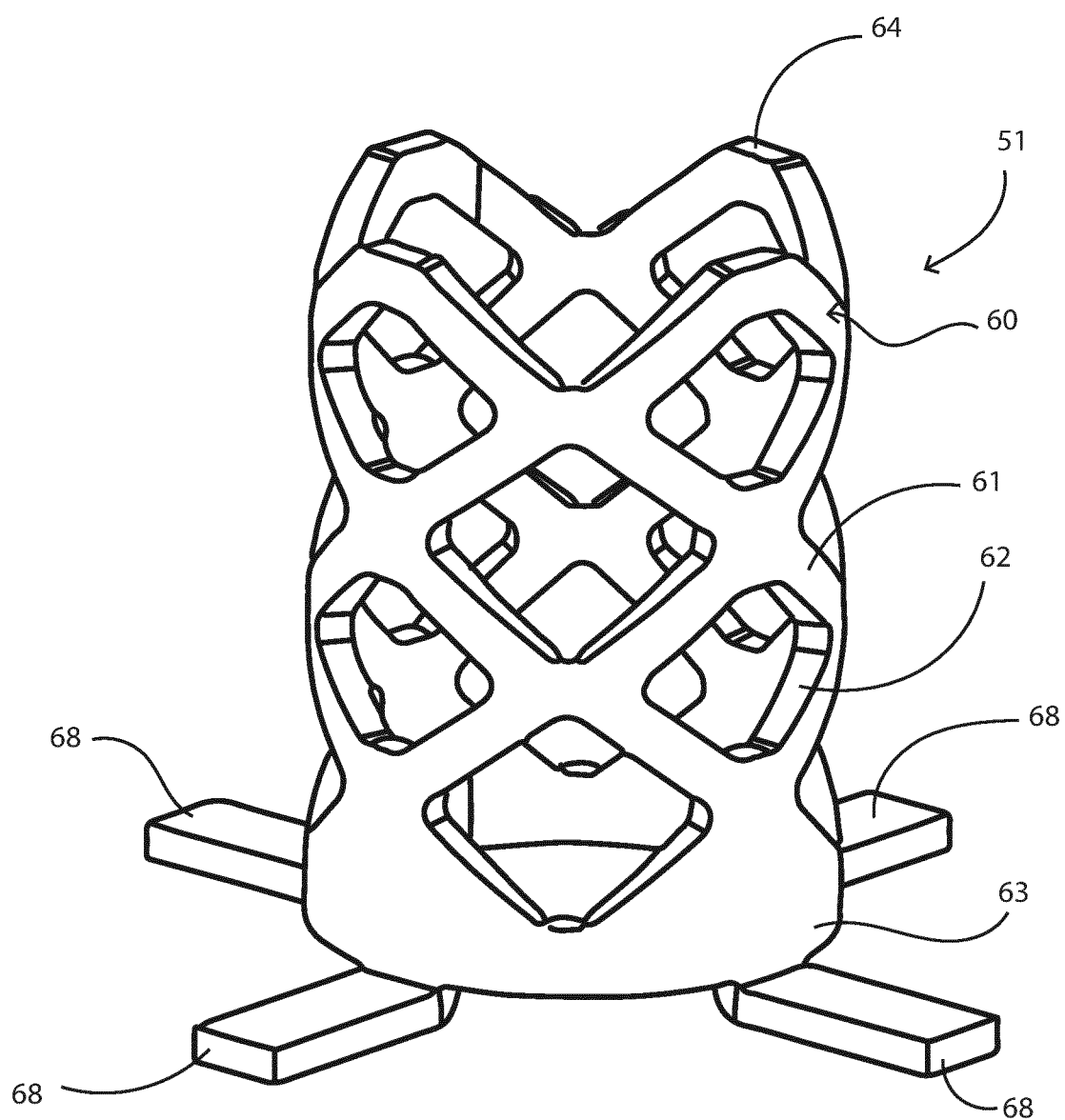
FIG. 3 is a perspective view of a scaffold or skeleton structure of the tube.

The scaffold structure 51 comprises, as shown in FIG. 3 a tubular mesh 60 comprising integral structural members 61 defining curved rectangular apertures 62. A proximal end of the tubular mesh 60 is of higher strength forming a rim 63 without apertures. The distal end of the tubular mesh 60 comprises distally-facing crowns 64 formed by distal members 64.

At the proximal end there are four metal spines 68 extending radially from the rim 63, at equal 90° radial separations. The spines 68 are integral with the tubular mesh 60.

Figure 4:
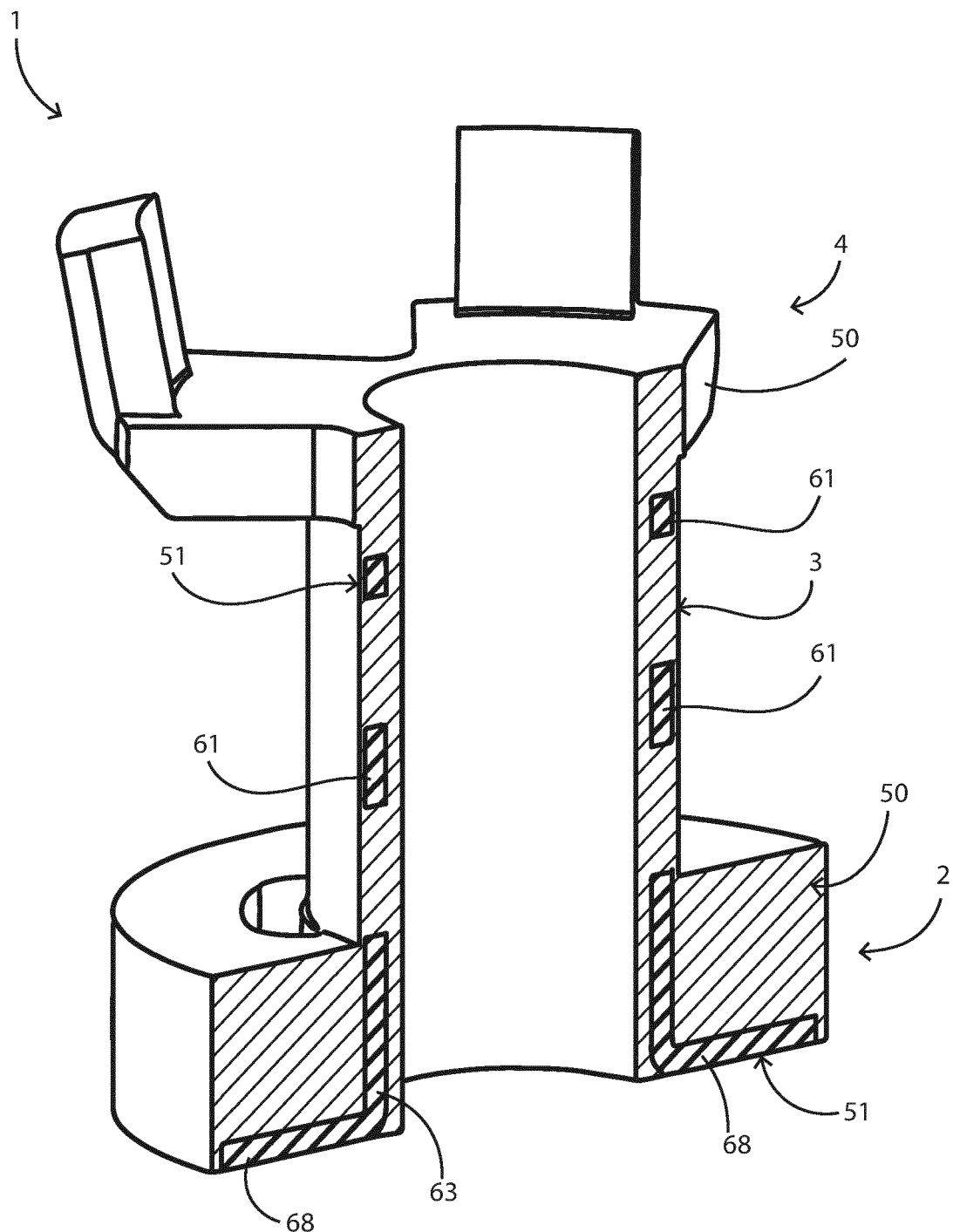
FIGS. 4 and 5 are cut-away views showing both the scaffold structure and the over-mould.
Figure 5:
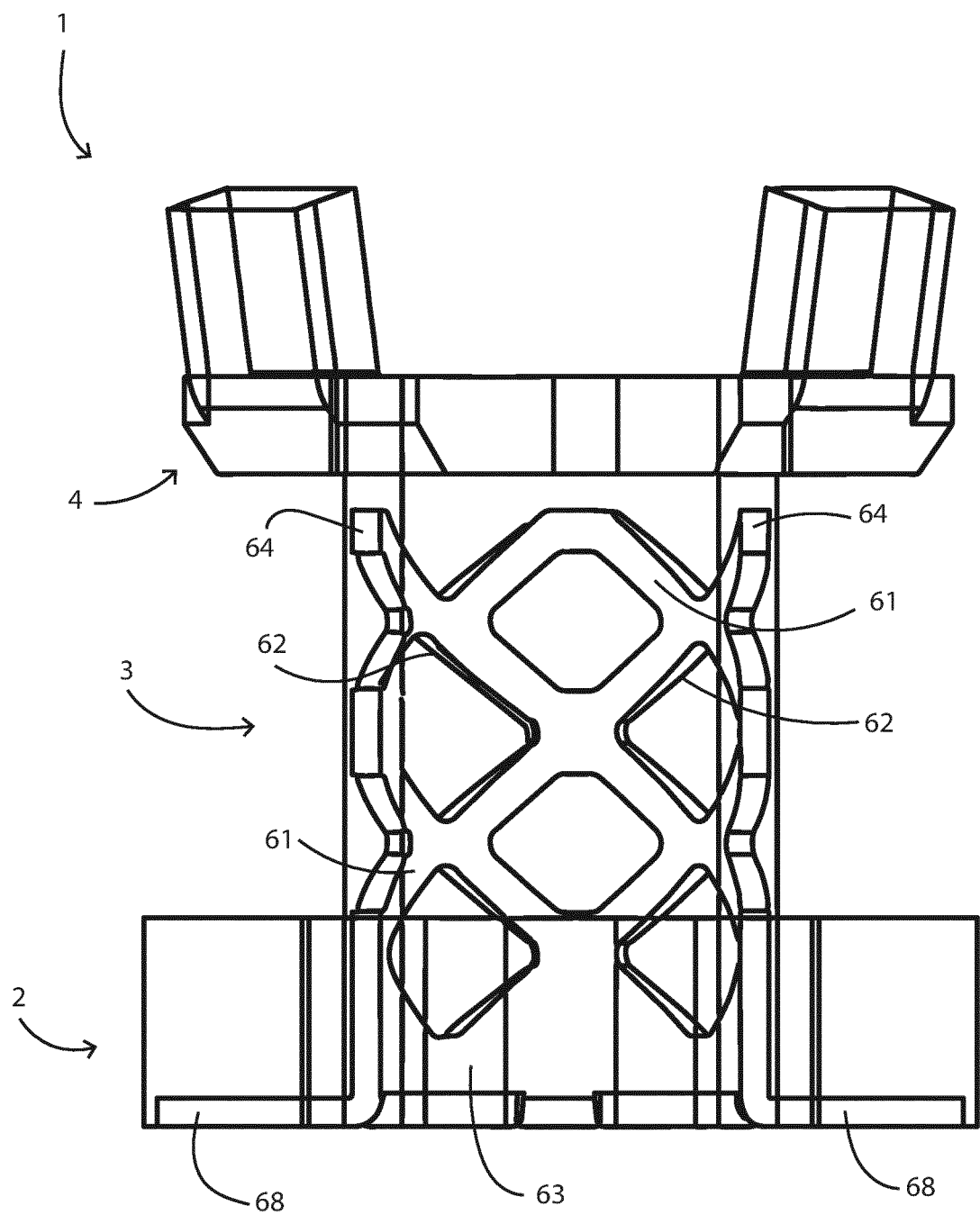

The tube is manufactured by fabricating the structure 51 using known techniques for fabricating stents. An example is laser-cutting a pattern and folding and welding. Another example is laser cutting from a tube with the correct internal diameter (ID) and wall thickness and then forming the legs post manufacture of the part. Then, the silicone 50 is over-moulded by injection moulding. The internal scaffold is placed and held in position in a mould and the silicone is injection-moulded over the scaffold. The over-moulding 50 is shown in more detail in FIGS. 4 and 5.

The manufactured tube 1 has excellent strength and flexural characteristics, with the proximal flange 2 having more rigidity than the distal flange 4 due to the metal spines 68. The inter-lumen connector 3 has excellent strength to remain open during deployment and after insertion for its life time, which can be up to approximately 2 years in one example, but it could be permanent in another example. The distal crowns 64 allow a configuration in the distal direction which facilitates insertion through the tympanic membrane with minimum resistance.

The tube 1 has a rigid structure except for the distal flange 4 with the stand-ups 20, which allows for effective installation into a tube delivery system, providing a folded narrow lead-in of the distal flange is desired. The rigid lumen and proximal flange allow for deployment of the tube without collapsing or deforming the tube. In-vivo, the scaffold structure ensures that the lumen remains intact throughout the lifetime of the device, whereas an all-silicone tube may kink or collapse due to external forces acting upon it.

CLINICAL BENEFITS

Silicone material is in contact with the body, while the tube has the underlying rigidity of a harder material such as a fluoroplastic or titanium or metal.

The scaffold structure ensures that the lumen will not collapse in-vivo and thus reduces the risk of tube blockage during use.

The scaffold structure gives rigidity to the proximal flange. The diameter of the distal flange of a tympanostomy tube is known to affect the rate of tube extrusion however it is also known that the proximal flange affects the rate of extrusion as the natural growth of the tympanic membrane pushes on the proximal flange, which causes the tube to extrude from the tympanic membrane over time. If, unlike the tubes described here, there were a more flexible outer (proximal) flange this may impair the body's ability to extrude the tube in a timely manner as the flexible proximal flange would deform rather than extruding from the tympanic membrane.

The more flexible distal flange and the inter-flange distance allows ease of tube placement, even in retracted ear drums because, as the distal (inner) flange deforms and opens it engages with the medial side of the tympanic membrane and deploys precisely in the incision.

The mechanical properties of the tube with silicone and Stainless Steel inner allows for flexibility in manufacture of tubes with other tube configurations, such as a T-Tube, which could be included in the device as an alternative tube choice for clinicians. Typically, a T-Tube has a very large distal (inner) flange (approx. 10 mm for example) and stays in the body for greater than 2 years and in some cases indefinitely.

Colour is readily added to silicone material—a blue colour for example allows the clinician to easily see the tube outer flange during intra-operative placement allowing for more accurate placement. Post operatively, the clinician can see the tube in situ more easily which can often be difficult when examining paediatric ears especially in small ears or a moving patient.

In cases where tubes do not extrude naturally, they have to be surgically removed. The silicone inner flange is flexible and therefore it may be easier and less traumatic to the tympanic membrane to remove this tube, when necessary. This may result in a reduced perforation rate.

The invention is not limited to the embodiments described but may be varied in construction and detail. It is envisaged that the tubular mesh structure member may have smaller or larger cross-sectional areas, depending on the clinical requirements. In some cases, there may be spines for the distal flange, and if so, they may be more flexible than the spines for the proximal flange by having a smaller cross-sectional area for example. There may be any desired number of spines for the proximal flange, and for the distal flange if they exist. The volume of outer material is chosen to ensure that the scaffold does not protrude in use, and of course according to other clinical requirements.

As noted above the tube may be for other in vivo medical applications such as fluid transfer between two biological structures which are separated by a thin membrane. However, it is particularly preferred for the tympanic membrane.

The tube may be referred to as a fluidic bridging tube, for transfer of any fluid, gas or liquid, including air for ventilation. Also, the scaffold structure may be configured for expanding during deployment, either self-expanding using a shape memory scaffold material such as nitinol or by applied pressure from within using for example a balloon.

Also, it is envisaged that the outer material is not over-moulded, and the scaffold structure may be embedded alternatively by for example press-fitting the scaffold structure into a tube or sleeve-shaped body of outer material. Also, it is envisaged that the outer material does not completely surround the scaffold structure.

It is envisaged that the tube and scaffold could be manufactured in a collapsed state. In one embodiment the scaffold material could be made from a stainless steel or titanium material which during deployment of the tube would utilize an expansion mechanism from within such as an inflatable balloon. In another embodiment the scaffold material could be made from a metal with shape memory properties which would expand once released from a retaining component of the device. In both of these embodiments, the silicone over-mould would expand with the expansion of the scaffold to the new larger size. These embodiments allow for a lower profile of device which would improve the ability to puncture the ear drum and visualization of the device during deployment. The flexible silicone material may in other examples be a suitable medical-grade flexible material such as a thermoplastic elastomer, "TPE".

The invention claimed is:

1. A fluidic bridging tube for use in a human or animal, the tube comprising a proximal flange, a distal flange, and an inter lumen connector with a lumen extending unobstructed from a proximal end of the proximal flange through a distal end of the distal flange, wherein the tube comprises a scaffold structure and an outer material fully surrounding the scaffold structure which is softer than the scaffold structure, wherein the distal flange does not include any part of the scaffold structure, and wherein the scaffold comprises a plurality of spines extending with a radial component at a proximal end of the scaffold structure into the proximal flange and configured to provide structural support to the proximal flange.

2. The fluidic bridging tube of claim 1, wherein the tube is a tympanostomy tube.

3. The fluidic bridging tube of claim 1, wherein the scaffold structure comprises a tubular mesh extending through at least some of the inter lumen connector.

4. The fluidic bridging tube of claim 3, wherein the tubular mesh comprises a member defining substantially curved rectangular mesh apertures.

5. The fluidic bridging tube of claim 4, wherein the substantially curved rectangular mesh apertures have substantially equal sides.

6. The fluidic bridging tube of claim 3 wherein the tubular mesh comprises, at its distal end, at least one distally facing crown comprising a vertex at its distal end the vertex extending farther in a distal, longitudinal direction than other portions of the distal end of the tubular mesh.

7. The fluidic bridging tube of claim 3, wherein the tubular mesh comprises a rim without apertures at its proximal end.

8. The fluidic bridging tube of claim 1, wherein the plurality of spines are disposed radially such that they are substantially equally separated.

9. The fluidic bridging tube of claim 1, wherein the scaffold structure is constructed from a material selected from Stainless Steel, Nitinol, titanium, or a polymer.

10. The fluidic bridging tube of claim 1, wherein the outer material comprises a medical grade flexible material.

11. The fluidic bridging tube of claim 10, wherein the medical grade material comprises a silicon rubber compound.

12. The fluidic bridging tube of claim 1, wherein the outer material is over-moulded on the scaffold structure.

13. The fluidic bridging tube of claim 1, wherein the scaffold structure is inflatable radially from within.

14. The fluidic bridging tube of claim 13, wherein the scaffold structure is inflatable radially from within by a balloon, and the outer material is configured to expand with expansion of the scaffold structure.

15. The fluidic bridging tube of claim 1, wherein the scaffold structure comprises a shape memory material configured to expand from a retaining component, and the outer material is configured to expand with expansion of the scaffold structure.

16. The fluidic bridging tube of claim 1, wherein the proximal flange has more rigidity than the distal flange.

17. The fluidic bridging tube of claim 1, wherein the scaffold structure is rigid.

* * * * *